(12) United States Patent
Thomas et al.

(10) Patent No.: US 12,290,425 B2
(45) Date of Patent: May 6, 2025

(54) LINT FREE CROSSLINKED CHITOSAN-PVA SPONGE AS AN ABSORBENT WOUND DRESSING AND METHOD OF PREPARATION THEREOF

(71) Applicant: Sree Chitra Tirunal Institute for Medical Sciences and Technology, Thirunananthapuram (IN)

(72) Inventors: Lynda Velutheril Thomas, Thiruvananthapuram (IN); Prabha Damodaran Nair, Thiruvananthapuram (IN); Nimi Nirmala, Thiruvananthapuram (IN); Shanti Krishna Ayilliath, Thiruvananthapuram (IN)

(73) Assignee: Sree Chitra Tirunal Institute for Medical Sciences and Technology, Thirunananthapuram (IN)

( * ) Notice: Subject to any disclaimer, the term of this patent is extended or adjusted under 35 U.S.C. 154(b) by 1203 days.

(21) Appl. No.: 16/959,143

(22) PCT Filed: Dec. 26, 2018

(86) PCT No.: PCT/IN2018/050879
§ 371 (c)(1),
(2) Date: Dec. 22, 2020

(87) PCT Pub. No.: WO2019/130348
PCT Pub. Date: Jul. 4, 2019

(65) Prior Publication Data
US 2021/0322225 A1 Oct. 21, 2021

(30) Foreign Application Priority Data
Dec. 29, 2017 (IN) .............. 201741047245

(51) Int. Cl.
| | | |
|---|---|---|
| *A61F 13/00* | (2024.01) | |
| *A61F 13/01* | (2024.01) | |
| *C08J 3/12* | (2006.01) | |
| *C08J 3/18* | (2006.01) | |
| *C08K 5/00* | (2006.01) | |
| *C08L 5/08* | (2006.01) | |
| *C08L 29/04* | (2006.01) | |

(52) U.S. Cl.
CPC .. *A61F 13/01012* (2024.01); *A61F 13/01017* (2024.01); *C08J 3/122* (2013.01); *C08J 3/18* (2013.01); *C08K 5/0016* (2013.01); *C08L 5/08* (2013.01); *C08L 29/04* (2013.01); *A61F 2013/00348* (2013.01); *C08L 2312/00* (2013.01)

(58) Field of Classification Search
CPC ...... A61F 13/00017; A61F 2013/00348; A61F 13/01012; A61F 13/01017; C08J 3/18; C08K 5/0016; C08L 5/08; C08L 29/04; C08L 2312/00
See application file for complete search history.

(56) References Cited

U.S. PATENT DOCUMENTS

2013/0052257 A1* 2/2013 Al Mousa ............. A61L 15/225
204/157.64

FOREIGN PATENT DOCUMENTS

| | | | | |
|---|---|---|---|---|
| JP | 2006045970 | * | 8/2007 | |
| WO | WO-2013096605 A1 | * | 6/2013 | ....... A61F 13/00004 |

OTHER PUBLICATIONS

Kouchak et al. (Iranian Journal of Basic Medical Sciences, vol. 17, No. 1, Jan. 2014 pp. 14-20). (Year: 2014).*
Changfeng Chen (International Journal of Biological Macromolecules 62 (2013) 188-193) (Year: 2013).*
Annabi et al. (Tissue Engineering Part B, vol. 16, No. 4, 2010, 371-383) (Year: 2010).*

* cited by examiner

Primary Examiner — Anna R Falkowitz
(74) Attorney, Agent, or Firm — Dinsmore & Shohl LLP

(57) ABSTRACT

This invention relates to a lint free absorbent wound dressing, comprising a plasticized blend of a natural biopolymer and poly vinyl alcohol mixed in an acidic solvent which is neutralized and crosslinked using green crosslinking buffer system, finding application in exudating and bleeding wounds.

Figure 1:

5 Claims, 2 Drawing Sheets

LINT FREE CROSSLINKED CHITOSAN-PVA SPONGE AS AN ABSORBENT WOUND DRESSING AND METHOD OF PREPARATION THEREOF

FIELD OF THE INVENTION

This invention relates to a lint free absorbent wound dressing and a process for the preparation thereof, in particular to a crosslinked Chitosan-PVA sponge as an absorbent wound dressing.

This invention further relates to a lint free absorbent wound dressing using the natural biopolymer based on chitosan and a synthetic polymer poly vinyl alcohol and the method of producing such dressings and the use of such dressings in different types of wounds like burn wounds, surgical wounds and acute exudating wounds. The main advantage of the invention is that the dressing has open pore structure providing good absorption characteristics and moisture retention which maintains a moist environment in the wound site and the non adherent property of the dressing helps in its ease of removal. Moreover, the antibacterial and antiseptic nature of cross linker aids in reducing bacterial colonisation and prevents from local wound infection. It has an added advantage of low cost, simple process and the obtained material can be tailored to different sizes so as to use on low to moderately exudating wounds, as nasal packings, burns and the like.

BACKGROUND OF THE INVENTION

US Patent (US 20150135644 A1) discloses a method of manufacturing a chitosan wound dressing that involves reacting chitosan fiber with anhydride and making acylated chitosan felt through a nonwoven process, and through cutting, packing and sterilizing processes. This process makes use of a non-woven fiber dressing.

European patent EP 0878204 A2 discloses a super absorbent wound dressing with the ability to absorb large amounts of wound fluids and water. For this purpose, a super absorbent fiber is used, preferably consisting of polyacrylonitrile. The absorptive power of this fiber is obtained by saponification of surface molecules of the fiber. This patent also deals with the use of fibrous meshes as wound dressing which may face problems in controlled scale up in the arrangement of fibers.

US Patent (US 20040030283 A1) discloses a disposable absorbent wound dressing comprising skin health treatment additives for the treatment and prevention of Stage I-IV partial and full thickness pressure wounds. The disposable dressings conform to the anatomical shape of the body of a human and are capable of absorbing large quantities of wound drainage or exudates. Such disposable dressings are low adherent and facilitate painless removal without disturbing a healing tissue bed. Additive comprises a therapeutically effective amount of lipids, triglycerides and vitamins in a triglyceride wax carrier which is coated on biocompatible polyurethane foam. The base part of the wound dressing is inert synthetic polyurethane based foam where the healing properties are provided as additives to the dressing.

WO 2003045294 A1 discloses an absorbent wound dressing containing a hydrogel layer the absorbent layer comprises a layer of hydrophilic foam, a superabsorbent, or a combination thereof wherein the hydrogel layer comprises a hydrogel material selected from polyurethane gels, biopolymer gels, carboxymethyl cellulose gels, hydroxyethyl cellulose gels hydroxypropyl methyl cellulose, modified acrylamides and mixtures thereof. This patent uses a wound dressing with a layered approach for attaining the specific properties.

US patent (US 20050080372 A1) discloses a wound dressing comprising a backing layer, an adhesive layer and an absorbent layer between the backing layer and the adhesive layer, wherein the adhesive layer secures the absorbent layer to the backing layer and that the adhesive layer is interrupted in at least one zone enabling a direct contact between the absorbent layer and the backing layer and exposing at least a part of the skin contacting surface of the absorbent layer, characterized in that at least the skin facing surface of the adhesive layer is provided with a nondetachable, non adhesive cover layer. This patent also provides information on a layered wound dressing and dressing has a non adhesive cover layer.

Patents (EP 0570430 B1 and WO 1992013576 A1) discloses a wound dressing for heavily exuding wounds comprises of hydrophilic foam having an absorptive capacity of at least 10 times its own weight. For use on bleeding wounds and/or to improve the absorptive capacity of the foam itself the foam may be impregnated with alginate which acts both as a hemostat and as an absorption improver. The dressing may include a backing layer which provides a barrier to microorganisms. The foam material is a hydrophilic polyether polyurethane foam material derived from a foamable composition comprising two different classes of polyol components wherein one of said classes of polyol components is a polyether polyol rich in ethylene oxide groupings (polyol 1) and wherein the other said class of polyol component is a branched ethylene oxide modified polyether polyol (polyol 2). This layer also brings out a layered approach for attaining the various properties.

US Patent US 20130052257 A1 discloses an antimicrobial hydrogel wound dressing is a swellable polymer gel made from about 7-9% (wt/vol) polyvinyl alcohol (PVA), preferably 8.9%, about 0.1% (wt/vol) polyvinyl pyrrolidone (PVP), and about 12% (wt/vol) agar, preferably 1%, the balance (about 90%) being distilled water, the foregoing contents being crosslinked by gamma radiation at a dose of about 30 kGy. An effective amount of a pair of antibiotics is added to the gel at room temperature. The antibiotics include about 10,000 IU of polymyxin B sulfate, and about 5 mg neomycin per gram of gel. The polymyxin provides effective protection against various forms of gram negative microorganisms, and the neomycin is a broad spectrum antibiotic that provides protection against various forms of gram positive microorganisms.

US Patent (U.S. Pat. No. 6,613,347 B2) discloses a PVA sponge with low durometer skin silicone wound dressing where the PVA sponge is washed free of formaldehyde, dried and hydrated and a thin coating of less than 1 mm low durometer silicone is applied to the surface of the sponge. The composite wound dressing allows moisture adsorption through the skin into the PVA sponge body but presents an outer surface precluding wound growth into the sponge material.

Chinese patent (CN 103083711 A) discloses a chitosan-iodine composite biological medical film which is formed by compounding a chitosan iodine polyvinyl alcohol layer, a porous polyurethane layer and a hydrophilic polyglutamic acid net shaped gel layer, wherein the porous polyurethane layer is compounded between the chitosan iodine polyvinyl alcohol layer and the hydrophilic polyglutamic acid net shaped gel layer. The three layers have different effects, the chitosan-iodine polyvinyl alcohol layer has the effects of killing bacteria, moisturizing and promoting healing; The porous polyurethane layer has the effects of dewatering, absorbing seepage and moisturizing; And the hydrophilic polyglutamic acid net-shaped gel layer has the effects of stopping bleeding, adsorbing the wound and converting the adsorbed seepage to the porous polyurethane layer. Here also this patent discloses a three layered wound dressing providing the various properties.

Chinese patent (CN 101381500 B) discloses a chitin/polyvinyl alcohol composite foam material. The compositions in weight percentage of the material are 1 to 15 percent of chitin, 5 to 30 percent of polyvinyl alcohol, 3 to 15 percent of inorganic acid, 3 to 15 percent of formaldehyde, 1 to 5 percent of foaming agent, and the balance being distilled water. The chitin/polyvinyl alcohol composite foam material has the advantages of low cost, environmental protection, simple technique and so on; as for the fact that both the polyvinyl alcohol and the chitin have good biocompatibility, the material obtained can be applied to wound dressing, negative pressure sealed conduction, hemostatic materials and so on; and as for the fact that the chitin has certain absorption capacity on heavy metal ions, the chitin/polyvinyl alcohol composite foam material can also be used as a porous absorption material in water treatment. In this patent, formaldehyde is used as the potential crosslinking agent which is toxic and has harmful effects.

Chinese Patent (CN 101974189 B) discloses a succinyl chitosan/polyvinyl alcohol composite sponge. The composite sponge is prepared with succinyl chitosan and polyvinyl alcohol as the raw materials and comprises the following raw materials by weight: 0.52% of succinyl chitosan, 9-10% of polyvinyl alcohol, 9-13% of inorganic acid, 10-17% of formaldehyde, 3-5% of foaming agent and the balance water. The method can prepare the composite sponge with higher water absorbing capacity, better flexibility and viscoelasticity and good biocompatibility and the advantages of low cost, environmental protection and simple process, and the obtained material can be applied to treating wound cavity infection, burns, skin grafting, etc. Here again the patent talks of the use of formaldehyde as the crosslinking agent which may elicit harmful responses if the washing steps are not appropriate.

European patent (EP 3087960 A1) discloses a 3 layered wound dressing comprising two outer layers fabrics and one middle layer fabric. The first outer layer and the second outer layer comprise at least one of the following fibres: alginate, chitosan, cellulose, carboxy methyl chitosan, acylated chitosan, carboxy methyl cellulose, carboxyethyl cellulose, water insoluble cellulose alkyl sulfonate, polyvinyl alcohol fibre, polypropylene, polyester, polyamide, or polyacrylonitrile. The middle layer comprises at least one of the following fibres: alginate, chitosan, cellulose, carboxymethyl chitosan, acylated chitosan, carboxymethyl cellulose, carboxyethyl cellulose, water insoluble cellulose alkyl sulfonate fibre, bicomponent fibre, polyvinyl alcohol, polypropylene, polyester, polyamide, polyacrylonitrile, crosslinked acrylates copolymer super absorbent fibres, and wood pulp. This patent discloses a layered fabric based system approach.

US Patent (US006022556A) discloses a water swellable wound dressing materials comprising from 5% to 50% of an alginate ester of a $C_1$-$C_6$ polyhydric alcohol; from 50% to 95% of a humectant consisting of one or more $C_1$-$C_6$ monohydric or polyhydric alcohols; and from 0% to 30% of water, the percentages being calculated by weight based on the weight of the material when anhydrous. The preferred alginate ester is propylene glycol alginate (PGA). The materials swell but do not dissolve in cold or warm water. Insolubility is achieved by the addition of polyvalent cations such as calcium ions, or by covalent cross-linking of the PGA, or by adding from 10 to 35% by weight of water-swellable polysaccharide such as gelatin, or by adding from 5% to 20% by weight of a cationic polymer such as chitosan. This patent discloses an alginate chitosan based system.

Chinese Patent (CN 102108172 A) discloses a chitosan/polyvinyl alcohol (PVA) porous composite material. The material is prepared from the following raw materials in percentage by weight: 1-5% of chitosan, 10-30% of PVA, 1-5% of acetic acid, 5-10% of inorganic acid, 5-10% of crosslinking agent, 6-10% of foaming agent, 0.5-2% of antibacterial agent, 1-5% of softening agent and the like. The obtained material has the characteristics of good biocompatibility, excellent antibacterial effect, strong liquid absorption capability, biodegradability, good adhesion to skin and the like, and has functions of rapid hemostasis, antibiosis, antiinflammation and acceleration of wound healing, thus the material is suitable for serving as various wound dressings. The crosslinking agent is formaldehyde, glyoxal, butyraldehyde, glutaraldehyde, polyaldehydes, epoxy chloropropane, citric acid, at least one of borax, or mixtures thereof. Here also this patent makes use of harmful crosslinking agents.

Patent Numbers (US 20140314706 A1, CA 2914610 A1) disclose a hemostatic putty for treatment of a variety of wounds topographies, including but not limited to highly three-dimensional wounds, for example gunshot wounds and impalements. The putty is comprised of a matrix polymer weakly crosslinked or not crosslinked such that a viscoelastic matrix is formed. The viscoelastic nature of the putty is tunable by the composition and enables the putty to conform to a variety of wound topographies. Likewise, a hemostatic polymer, for example chitosan or hydrophobically modified chitosan, is included in this matrix to impart hemostatic properties and tissue adhesive on the putty. The hemostatic polymers disclosed prevent microbial infection and are suitable for oxygen transfer required during normal wound metabolism. The composition of the putty comprises a hemostatic biopolymer based on chitosan, a secondary polymer Poly vinyl alcohol, an ionic crosslinker like borates, and a solvent. The above disclosed patent makes use of chitosan-polyvinyl alcohol composite mixture in the form of putty which may be difficult to handle and remove as the stability of the putty is not fully discussed in this patent.

U.S. Pat. No. 4,572,906 discloses a chitosan based wound dressing, particularly useful for the protection of wounds during the healing process. The dressing comprises a blend of gelatin and chitosan in a weight ratio of about 3:1 to 1:3 and a compatible plasticizer in an amount of 0-40% w/w based on the combined weight of gelatin and chitosan. The patent discloses a blend of chitosan and gelatin and an adherent wound dressing and no claim is made on the absorbent property.

Patent WO 2003057267 A1 discloses a bandage of the type used on acute wounds, minor wounds, burn wounds and irritations, includes a first layer for covering the wound site and an area around the wound site, with the first layer including a top surface and bottom surface; a second layer over the first layer bottom surface, for absorbing exudates from the wound site; the second layer including a poly (ethylene oxide)-based compound and a chitosan-based compound. A third layer is situated over the second layer, the third layer being of a perforated film, and wherein, at least one antimicrobial agent is associated with the bandage in a position where the antimicrobial agent will come in contact with the wound site, and which is transferable from the bandage to the wound site, upon contact with the wound site. This patent discloses a layered wound dressing with an added antimicrobial agent.

Patent WO 2008019498 A1 discloses a compression bandage for the treatment of pain and inflammation, comprising a support substrate and an interpenetrating network of PVA disposed within the support substrate. The bandage provides cooling and delivery of therapeutic compounds. The bandage comprises an open cell foam matrix carrying an incorporated PVA hydrogel and optionally at least one additional therapeutic agent. The substrate is selected from the group consisting of a non-woven pulp-based, air-laid material, a biodegradable synthetic polymer system, natural fibrous material, hemp, cotton, bamboo, alginate, polyamides with high absorption, and an open cell polymer network. This patent also discloses a layered approach and the therapeutic compounds are incorporated.

OBJECTS OF THE INVENTION

It is therefore an object of this invention to propose a lint free absorbent wound dressing and a process for the preparation thereof.

It is a further object of this invention to propose a lint free absorbent wound dressing which is biocompatible and has very high rate of absorption towards blood, water and tissue fluids, and can be used as a wound dressing material for burns, surgical or other wounds, ulcers, etc.

Another object of this invention is to propose a lint free absorbent wound dressing which does not shed any lint on application to the intended site.

Yet another object of this invention is to propose a lint free absorbent wound dressing which has a non bioadhesive nature to alleviate the pain and discomfort caused due to its removal.

A further object of this invention is to propose a lint free absorbent wound dressing which is prepared with non toxic crosslinkers and plasticizers.

A still further object of this invention is to propose a wound dressing that is pliable and can be used to stuff deep wounds and orifices without disintegrating and can be easily removed after use.

These and other objects and advantages of the invention will be apparent from the ensuing description when read in conjunction with the accompanying drawings.

BRIEF DESCRIPTION OF THE ACCOMPANYING DRAWINGS

Figure 2:
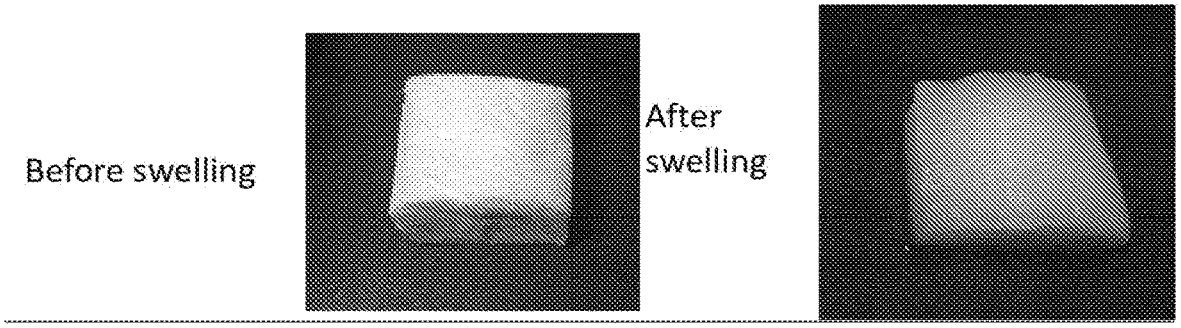
Figure 3:
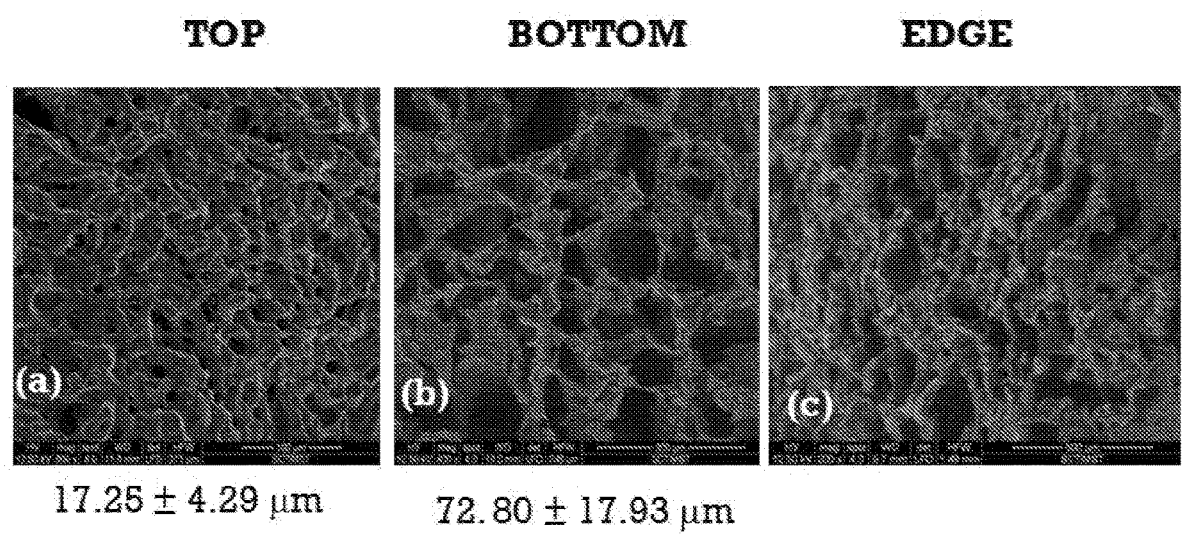

FIG. 1: Image of the freeze dried wound dressing.
FIG. 2: Fluid absorption capacity of the wound dressing
FIG. 3: Scanning electron microscopy (SEM) images of the dressing

SUMMARY OF THE INVENTION

The present invention relates to a lint free absorbent wound dressing using the natural biopolymer Chitosan and Poly vinyl alcohol and the method of producing such dressings and the use of such dressings in different types of wounds like burn wounds, surgical wounds and ulcers and as a packing in nasal surgeries. The dressing material comprises a combination of properties imparted by individual polymers, the antibacterial biodegradable polymer chitosan and a non adhesive hydrophilic synthetic polymer polyvinyl alcohol.

BRIEF DESCRIPTION OF THE INVENTION

This invention relates to a lint free absorbent wound dressing, comprising a plasticized blend of a natural biopolymer and poly vinyl alcohol mixed in an acidic solvent which is neutralized and crosslinked using green crosslinking buffer system, and finds application in exudating and bleeding wounds. The blend has a composition in weight percentage of 0.25 to 5 weight/vol % of chitosan, 2 to 10 weight/volume % of Polyvinyl alcohol and 1 to 2.5 vol/vol % of plasticizer. The wound dressing is a freeze dried sponge with a density ranging from 0.5 $g/cm^3$ to 6 $g/cm^3$.

This invention further relates to a process for the preparation of the wound dressing, comprising the steps of preparing an aqueous solution of polyvinyl alcohol (PVA) and preparing a solution of a biopolymer in acid/water mixture, followed by mixing the PVA solution with the biopolymer solution to obtain a blend, adding a plasticizer to the blend followed by adding a crosslinking agent and thoroughly mixing the same to obtain a final solution, subjecting said final solution to lyophilisation to obtain the wound dressing material.

In accordance with a further embodiment, this invention relates to a process for the preparation of the wound dressing, comprising the steps of preparing an aqueous solution of polyvinyl alcohol (PVA) and preparing a solution of a biopolymer in acid/water mixture, followed by mixing the PVA solution with the biopolymer solution to obtain a blend, optionally adding a plasticizer to the blend and thoroughly mixing the same to obtain a final solution, subjecting said final solution to lyophilisation to obtain a sponge, followed by soaking said sponge in a solution of a crosslinking buffer agent, washing and lyophilisation to obtain the wound dressing material.

The natural biopolymer has a viscosity ranging from 200 to 2000 CPS.

DETAILED DESCRIPTION OF THE INVENTION

Thus according to this invention is provided a lint free absorbent wound dressing, comprising a plasticized blend of a natural biopolymer and poly vinyl alcohol mixed in an acidic solvent which is neutralized and crosslinked using green crosslinking buffer system, finding application in exudating and bleeding wounds.

According to this invention is provided a process for the preparation of the wound dressing comprising the steps of preparing an aqueous solution of polyvinyl alcohol (PVA) and preparing a solution of a biopolymer in acid/water mixture, followed by mixing the PVA solution with the biopolymer solution to obtain a blend, adding a plasticizer to the blend followed by adding a crosslinking agent and thoroughly mixing the same to obtain a final solution, subjecting said final solution to lyophilisation to obtain the wound dressing material.

In accordance with a further embodiment, this invention relates to a process for the preparation of the wound dressing, comprising the steps of preparing an aqueous solution of polyvinyl alcohol (PVA) and preparing a solution of a biopolymer in acid/water mixture, followed by mixing the PVA solution with the biopolymer solution to obtain a blend, optionally adding a plasticizer to the blend and thoroughly mixing the same to obtain a final solution, subjecting said final solution to lyophilisation to obtain a sponge, followed by soaking said sponge in a solution of a crosslinking buffer agent, washing and lyophilisation to obtain the wound dressing material.

In accordance with this invention is provided a lint free absorbent wound dressing using the natural biopolymer Chitosan and Poly vinyl alcohol and the method of producing such dressings and the use of such dressings in different types of wounds like burn wounds, surgical wounds and ulcers and as a packing in nasal surgeries. The dressing material comprises a combination of properties imparted by the individual polymers, the antibacterial biodegradable polymer chitosan and a non adhesive hydrophilic synthetic polymer polyvinyl alcohol. The main advantage of the invention is that the dressing has open pore structure providing good absorption characteristics and moisture retention which maintains a moist environment in the wound site and the non adherent property of the dressing helps in its ease of removal. Moreover, the antibacterial and antiseptic nature of cross linker aids in reducing bacterial colonisation and prevents from local wound infection.

Chitosan is derived from chitin using various processes of sodium hydroxide washing to obtain the desired degree of deacetylation and molecular weight.

Chitosan is a biodegradable, nontoxic, complex carbohydrate derivative of chitin (poly-β-1, 4-D-glucosamine), and a naturally occurring substance. Chitosan is the deacetylated form of chitin. In general, the generic term chitosan is applied when the extent of deacetylation is above 70% and the generic term chitin is used when the extent of deacetylation is insignificant, or below 20%.

With less than 100% deacetylation, the chitosan polysaccharide is a linear block copolymer containing both N-acetyl-D-glucosamine and D-glucosamine monomer units. In its acid salt form, chitosan demonstrates mucoadhesive activity, which makes it an ideal candidate for consideration as a hemostatic agent.

The polycationic nature of chitosan also allows explaining chitosan analgesic effects. Indeed, the amino groups of the D-glucosamine residues can protonate in the presence of proton ions that are released in the inflammatory area, resulting in an analgesic effect too.

However due to the mucoadhesive nature of chitosan, wound dressings made of chitosan is associated with painful removal as the dressing tends to stick to the wound surface and on absorption tends to loose its structural stability.

The natural biopolymer chitosan can be used in its native form or a modified chitosan from the group consisting of chitosan acetate, chitosan lactate, carboxymethyl chitosan, chitosan glycolate, chitosan maleate and other substituted chitosan and its salts thereof can be used to prepare the sponge dressing. Chitosan is derived from chitin using various processes of sodium hydroxide washing to obtain the desired degree of deacetylation and molecular weight. Chitosan is a biodegradable, nontoxic, complex carbohydrate derivative of chitin (poly-β-1, 4-D-glucosamine), a naturally occurring substance. Chitosan is the deacetylated form of chitin. In general, the generic term chitosan is applied when the extent of deacetylation is above 70% and the generic term chitin is used when the extent of deacetylation is insignificant, or below 20%.

The polyvinyl alcohol is the synthetic polymer used where the molecular weight is usually in the range of 60000 to 200000 Mn. Polyvinyl alcohol (PVOH) is a hydrophilic linear polymer which forms copolymers of vinyl alcohol and vinyl acetate. Hence, the structural properties of polyvinyl alcohol polymers depend on the extent of polymerization and hydrolysis. The degree of hydrolysis ranges from 98-99.9%. PVA is an atactic material that exhibits crystallinity. PVA is composed mainly of 1,3-diol linkages [—CH2—CH(OH)—CH2—CH(OH)—] with a few percent of 1,2-diols [—CH2—CH(OH)—CH(OH)—CH2—]. PVA has a melting point of 230° C. and 180-190° C. (356-374 degrees Fahrenheit) for the fully hydrolyzed and partially hydrolyzed grades, respectively. It decomposes rapidly above 200° C. as it can undergo pyrolysis at high temperatures.

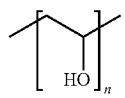

The lint free absorbent dressing was prepared by blending the two polymers in weight percentage of 0.25 to 5 weight/vol % of chitosan, 2 to 10 weight/volume % of Polyvinyl alcohol and 1 to 2.5 vol/vol % of plasticizer and the rest of the volume being water.

The plasticizer for plasticizing the blend in order to obtain soft and pliable sponge is selected from the group consisting of glycerol, sorbitol, propylene glycol, ethylene glycol, or polyethylene glycol or mixtures thereof. This helps to provide the appropriate softness which also contributes to the pliability of the sponge dressing.

The blend is prepared in an acid/water mixture where the concentration of the acid ranges from 0.5 to 1.5% vol/vol.

The dressing is then prepared using the process of lyophilization where the lyophilization process involves freezing the blend in the range of −20° to −30° and the drying phase ramped up to a temperature of 40° C. with the whole lyophilization cycle ranging from 24 to 45 hours based on the feed volume to obtain cellular structured dressings.

The dressing is crosslinked using green crosslinking buffer system and avoiding the use of any harmful crosslinking agents. The buffer is selected from the group consisting of salts of borates, polyphosphates, sulphates or sulphites and citric acid or mixtures thereof which is dissolved in a buffer with a final pH ranging from 8-10. The cross linkers may be added before the lyophilization step or after the lyophilization is over.

The lyophilization process gives rise to a highly open cellular structure wherein the % simulated wound fluid uptake is 1500-3000 wt %.

The other main advantage of the invention is that the dressing has open pore structure providing good absorption characteristics and moisture retention which maintains a moist environment in the wound site and the non adherent property of the dressing helps in its ease of removal.

The effect of inherent antimicrobial property of the polymer along with an antimicrobial agent as cross linker helps the dressing to restrain or kill the growth or replication of a broad spectrum of microbes and thereby preventing local wound infection.

The invention will now be explained in greater details with the help of the following non-limiting example which illustrate the development of a lint free absorbent dressing.

EXAMPLE

Example 1: Chitosan-PVA Sponge Using Borate Crosslinking 2.5% PVA solution is prepared in distilled water heating at 80° C., under magnetic stirring for 3 h. 2% Chitosan is prepared in 0.75% acetic acid aqueous solution under mechanical stirring for 3 h. Chitosan and PVA solutions are mixed in the ratio of 2:1 via mechanical stirring for an hour. 3% borax solution and 0.75% glycerol added to the solution, stirring continued 30 minutes. Final solution is subjected to freezing at −30° C. for 8.3 hours, followed by primary drying with the temperature ramping at a rate of 4° C./min up to 40° C. The final drying is at 40° C. for 5 minutes. 1 cm×1 cm samples were cut from the dressing and Weight of the sample noted down. Thickness of the sample measured. Density was calculated as follows, Density(g/cm3)=weight/width×length×thickness Density was measured with 5 samples at least. The density if the sample is 0.06±0.012 g/cm³

Example 2: Measurement of the Fluid Absorption Capacity

The fluid absorption capacity (FAC) and moisture vapor transmission rate (MVTR) of the wound dressing was evaluated using simulated wound fluid as per British Pharmacopoeia standards. For determining the fluid absorbing capacity, dressing of size 1 cm×1 cm and known weight were placed into beakers of the test solution. The dressing samples were removed from the solution at interval of 24 hour and gently blotted to remove excess liquid from the outer surface and then reweighed. The Fluid absorption of the dressing samples was calculated by the following equation:

Absorption rate=$W_s - W_d$ g/cm/day $$\text{Fluid absorption capacity (\%)} = \frac{(W_s - W_d)}{W_d} \times 100$$

where $W_d$ and $W_s$ represent the weight of the dressing samples in dry and swollen states.

The fluid absorption rate of the dressing is 0.63±0.13 g/cm2/day and Fluid absorption capacity (%) is 2881±581%

Example 3: Measurement of Moisture Vapor Transmission Rate (MVTR)

The Moisture Vapor Transmission Rate (MVTR) of the dressings was determined as per the standard test method (ASTM E96). The samples were cut in a circular shape with a diameter of 3 mm greater than the diameter of the bottle. The sample thus cut is used as a cap on the mouth of the plastic bottle. The samples were sealed to bottle using a suitable adhesive agent. The setup is weighed and kept at 37° C. in an incubator for 24 hours. The loss in weight because of passage of moisture vapor through the membrane was determined by the difference. The MVTR (g/m2/h) was calculated by the following equation:

MVTR=Change in mass of the vials with the sample/Area×24 h

The fluid handling capacity (FHC; g/10 cm²) of the dressing samples was calculated as the sum of the weight of the test solution retained by the dressing samples (Fluid absorption) and the weight of the fluid lost by vapor transmission through the dressing (MVTR).

The moisture vapour transmission rate (MVTR) of the dressing is 0.02±0003 g/cm²/day and the fluid handling capacity is 0.55±0.30

Example 4: Measurement of the Wet Strength of the Scaffold

The evaluation of scaffolds mechanical behavior was performed using the tensile test equipment Universal Instron 5882 machine and a load cell of 5 kN and test speed of 0.5 mm/min at 25° C. and according to ASTM D 695 (Standard Test Method for Compressive Properties of Rigid Plastics). Rectangular samples with 10 cm length and 2 cm in width was used for the study and was prewet with simulated wound fluid before testing.

The tensile strength of the dressing is 0.02284±0.007 MPa with a maximum load of 1.42±0.47 N

Experiment 5: Probing the Surface of the Dressing Using Scanning Electron Microscopy (SEM)

The surface morphology of the sample was studied after critical point drying and gold coating. The samples were cut by 0.5×0.5 cm, critical point dried (Hitachi HCP-2, Hitachi, Japan), gold sputtered in vacuum (Hitachi E101), and examined by means of secondary imaging under a 15 kV scanning electron microscope (Hitachi S 2400) for observation of pore morphology on both the top and bottom surfaces. The average pore size for the pores on top was found to be 17.25±4.29 μm and average pore size on bottom surface is 72.8±17.93 μm.

Example 6: Mucoadhesion Assay for Ascertaining Bioadhesive Strength

Mucoadhesion was tested using the TA-XTPlus texture analyzer equipped with a 5 kg load cell by dropping the probe (7 mm Domical Stainless steel probe) down onto the adhesion surface at 0.5 mm/sec, applying 500 grams of force for 10 seconds, and then retracting the probe at 0.5 mm/sec while measuring the downward pulling reaction force on the probe upon retraction due to adhesion. The mucoadhesion probe was prepared by placing a 1 cm diameter sample by using a two side tape onto the probe surface. The probe which is then run through adhesion testing against the prepared sample of goat loin meat just below the skin surface wetted with phosphate buffered saline (pH 7.4) which is attached to the lower end of the probe (θ:12.5 mm) of the instrument with two sided tape. A delay period of 15 sec was allowed between the two compressions. A positive force peak upon probe retraction due to the adhesion was recorded and noted. The maximum detachment force, as a function of displacement, was recorded. The test was conducted at 37° C. and each experiment was carried out six times.

The Force of adhesion of dressing=191.46±15.52 mN

Example 7: Another Process of Absorbent Chitosan-PVA Sponge Crosslinked in Green Buffer Crosslinking Agent is Described Below 5% PVA solution is prepared in distilled water heating at 80° C.; under magnetic stirring for 3 h. 2% Chitosan is prepared in 1% acetic acid aqueous solution under mechanical stirring for 3 h. Chitosan and PVA solutions are mixed in the ratio of 2:1 via mechanical stirring for an hour. 0.75% glycerol added to the solution, stirring continued 30 minutes. Final solution is subjected to freezing at −30° C. for 12 hours, followed by primary drying with the temperature ramping at a rate of 4C/min up to 25° C. The crosslinking buffer with pH 9.5 is prepared with a mixture of 7.5% w/v Sodium tripolyphosphate, 2% Borax and 4% citric acid. The sponge is then soaked in the crosslinking buffer for 1 hour and then washed and again subjected to a small lyophilisation cycle of total 16 hours. The sponge is then subjected to absorption and Moisture Vapor Transmission Rate (MVTR) studies.

Example 8: Another Process of Preparation of Absorbent Chitosan-PVA Sponge by Sodium Sulphate Cross Linking is Described Below PVA solution (5%) was prepared by heating at 80° C. for 3 h. Then 2.5% chitosan solution was prepared in presence of 1% acetic acid. The two solutions having equal proportions were blend to get a homogeneous solution mixture. Then the solution mixture was freezed at −20° C. and lyophilized. The sponge thus obtained was crosslinked using an antimicrobial cross linking agent sodium sulphate in KOH coagulation bath for 1 h. Then it was washed thoroughly to attain a neutral pH and was frozen at −20° C. and lyophilised to get the highly absorbing and non adhesive sponge.

The present invention provides a lint free crosslinked Chitosan-PVA sponge as an absorbent wound dressing and method of preparation thereof. The lint free wound dressing is prepared through a controlled lyophilization cycle comprising a plasticized blend of a natural biopolymer and poly vinyl alcohol. The polymers are mixed in an acidic solvent which is neutralized and crosslinked using green crosslinking buffer system for use as an absorbent wound dressing in exudating and bleeding wounds and have ability to stuff deep wounds and orifices. The dressing provides good absorption capacity of 500-800 weight %. It is pliable with low bio adhesiveness and hence does not stick to the wound surface and can alleviate the pain and discomfort suffered by patients due to its painless removal. It has an added advantage of low cost and simple process of development. The dressing may also have a breathable backing layer support.

The problem of painful removal of wound dressing is solved by blending PVA with chitosan to get dressings with low bioadhesive strength. The problems faced during stuffing or contouring dressings in deep wounds is solved by preparing a composition that is highly pliable and can be folded for use. The process also avoids the use of harmful crosslinking agents in preparing the dressing and uses non toxic green crosslinking buffer systems. By the use of controlled lyophilization cycles to get controlled pore sizes for optimum absorption, optimum absorption of exudates and wound fluid is achieved.

We claim:

1. A process for the preparation of a cellular structured wound dressing consisting of the steps of:
    preparing an aqueous solution of polyvinyl alcohol (PVA) and preparing a solution of a biopolymer in acid/water mixture, followed by mixing the PVA solution with the biopolymer solution to obtain a blend,
    adding a plasticizer to the blend followed by adding a crosslinking agent and thoroughly mixing the same to obtain a final solution,
    subjecting said final solution to lyophilization to obtain a sponge,
    wherein lyophilization involves a step of freezing the blend in a range of −20° C. to −30° C. followed by drying with a temperature ramping at a rate of 4° C./min up to 40° C. to obtain cellular structured wound dressings; wherein the biopolymer is a chitosan having viscosity in the range from 200 to 2000CPS;
    the crosslinking agent is a salt of borate or polyphosphates or sulphates or sulphites or citric acid or a mixture thereof; and
    the plasticizer is glycerol;
    wherein the cellular structured wound dressing is with a density ranging from 0.5 g/cm$^3$ to 6 g/cm$^3$.

2. The process as claimed in claim 1, wherein said blend is prepared in an acid/water mixture where the concentration of the acid ranges from 0.5 to 1.5%.

3. The process as claimed in claim 1, wherein the crosslinking agent is a buffer with a final pH ranging from 8-10.

4. The process as claimed in claim 1, wherein an amount of chitosan present in the obtained blend is in the range of 0.25 to 5 weight/vol %, an amount of PVA present in the obtained blend is in the range of 2 to 10 weight/volume %, and an amount of plasticizer present in the obtained blend is in the range of 1 to 2.5vol/vol %.

5. The process as claimed in claim 1, wherein the PVA has a molecular weight in the range of 60,000 to 2,00,000 Mn and a degree of hydrolysis in the range of 98-99.9%.

* * * * *